United States Patent [19]

Imagawa et al.

[11] Patent Number: 5,627,645
[45] Date of Patent: May 6, 1997

[54] METHOD OF AND APPARATUS FOR MEASURING RETARDATION OF COMPOSITE LAYER

[75] Inventors: Kyoji Imagawa, Hyogo; Shinichi Nagata, Osaka; Kiyokazu Sakai, Hyogo, all of Japan

[73] Assignee: New Oji Paper Co., Ltd., Tokyo, Japan

[21] Appl. No.: 533,715

[22] Filed: Sep. 26, 1995

[30] Foreign Application Priority Data

Sep. 30, 1994 [JP] Japan .................... 6-238263

[51] Int. Cl.$^6$ .................... G01N 21/21
[52] U.S. Cl. .................... 356/364; 356/367
[58] Field of Search .................... 356/364, 365, 356/366, 367, 33, 34, 35

[56] References Cited

U.S. PATENT DOCUMENTS

| | | | |
|---|---|---|---|
| 2,244,362 | 6/1941 | Hartig | 356/367 |
| 3,724,952 | 4/1973 | Vossberg | 356/366 |
| 4,850,710 | 7/1989 | Mochida et al. | 356/367 |
| 4,973,163 | 11/1990 | Sakai et al. | 356/35 |
| 5,005,977 | 4/1991 | Tomoff | 356/367 |

*Primary Examiner*—Richard A. Rosenberger
*Attorney, Agent, or Firm*—Nikaido, Marmelstein, Murray & Oram LLP

[57] ABSTRACT

A compensation polarizing plate which is superior in polarization characteristic to a polarizing filter layer of a composite layer sample is arranged on the polarization filter layer side of the composite layer sample whose polarizing filter layer has an insufficient degree of polarization, and polarization transmission axes of the polarizing filter layer and the compensation polarizing plate are kept in parallel with each other to compensate the polarization characteristics of the polarization filter layer. Measurement for obtaining the retardation value and the optical principal axis direction of the sample is carried out in the state of the compensated sample.

12 Claims, 4 Drawing Sheets

METHOD OF AND APPARATUS FOR MEASURING RETARDATION OF COMPOSITE LAYER

BACKGROUND OF THE INVENTION

1. Field of the Invention

The present invention relates to a method of and an apparatus for measuring retardation of a composite layer sample such as a composite sheet prepared by stacking a polarizing film and a phase difference film (retardation film) with each other to be applied to a liquid crystal display panel, for example.

2. Description of the Background Art

As liquid display elements are increasingly employed, requirements for large areas of liquid crystal display panels and enlargement of ranges of visual directions are also increased. Thus, awaited is development of a technique which can readily measure characteristics of a film type polarizing filter (polarizing film) and a phase difference film in steps of producing such films.

In general, the display panel of a liquid crystal display unit has a polarizing filter which is provided on one surface of a liquid crystal cell sealing a liquid crystal material therein as an optical element and a phase difference film, a polarizing filter and a protective film which are successively stacked on another surface (observed side). The phase difference film, which is adapted to compensate polarization characteristics of the liquid crystal cell, consists of a birefringent material. It is necessary to examine the states of a composite sheet, also called an elliptic polarizing plate, which is obtained by stacking and bonding the polarizing filter and the phase difference film with each other, such as the polarization transmission axis direction of the polarizing filter, the optical principal axis direction of the phase difference film and the retardation value thereof. We refer to these characteristic (i.e., retardation value etc.) as "optical characteristic" hereafter.

In the display panel of the liquid crystal display unit, the optical characteristic as viewed from a direction other than that perpendicular to the surface, i.e., the optical characteristic obtained with changing the incident angle of measuring beam, is also an important characteristic. In order to evaluate the angle of visibility, it is necessary to measure the retardation value in the case of changing the angle of incidence of a measuring beam in the state of the composite sheet. At present, however, white light is introduced into the composite sheet to make evaluation by the spectrum of the transmitted light.

SUMMARY OF THE INVENTION

The inventors of the present invention also described a method of measuring retardation of a composite layer sheet of a polarizing film and a phase difference film in Japanese Patent Laying-Open Gazette 6-317519 (1994). From the result of measurement of various kinds of composite layer samples, it is found that some samples could be measured with high accuracy while some samples could not be measured with high accuracy. From further investigation, the following fact was found out. It is possible to obtain the aforementioned measurement values with accuracy when the degree of polarization of the polarizing filter which is employed for the composite sheet is in excess of about 99%. When the degree of polarization is insufficient (e.g., less than 99%), however, the calculation results of the optical principal axis direction and the retardation value are extremely dispersed to cause reduction of the measuring accuracy and an unmeasurable situation as the case may be.

In the method of evaluating the angle of visibility of the composite sheet by a spectral method, it is not easy to express the evaluation results in figures and hence it is difficult to provide objective evaluation criteria.

A first object of the present invention is to provide a method and an apparatus which can correctly measure the optical principal axis direction and the retardation value of a composite layer sample including a polarizing filter layer and a birefringent layer, also when the degree of polarization of the polarizing filter layer is insufficient.

A second object of the present invention is to make it possible to evaluate the visibility also in the case of such a composite layer sample.

According to the present invention, a composite layer sample obtained by stacking a polarizing filter layer and a birefringent layer is provided on the polarizing filter layer side with a compensation polarizing plate, while polarization transmission axes of the polarization filter layer and the compensation polarizing plate are kept in parallel with each other to compensate the polarization characteristic of the polarizing filter layer. In measurement of the retardation value etc., a measuring beam is applied from the side of the compensation polarizing plate to pass light transmitted through the compensation polarizing plate and the composite layer sample through an analyzer, whose polarization direction is relatively rotated with respect to that of the composite layer sample for obtaining the relation between the intensity of the light transmitted through the analyzer and the polarization orientation of the analyzer. Thus, the measurement accuracy is extremely improved.

The measurement of the retardation value etc. includes both of the case of applying the measuring beam in unpolarized condition to the compensation polarizing plate without through a polarizer, and the case of arranging a polarizer which is kept in a prescribed polarization orientation relation such as a parallel Nicol state with the analyzer on the light incidence side of the compensation polarizing plate for applying the measuring beam to the compensation polarizing plate through the polarizer. That is, in the former case, the polarizer is not used.

In order to make it possible to evaluate visibility, a surface of the composite layer sample is first arranged in a state perpendicular to the optical path of the measuring beam and the polarization direction of the analyzer is relatively rotated with respect to that of the composite layer sample to obtain the retardation value and the optical principal axis direction of the composite layer sample. The optical principal axis is the main refringence direction, while there are two directions having the maximum and minimum refractive indices and these two directions are perpendicular to each other. Either one of the two optical principal axis directions is employed as an inclination axis to incline the surface of the composite layer sample and the polarization direction of the analyzer is again relatively rotated with respect to that of the composite layer sample to detect the relation between intensity of light transmitted through the analyzer and the polarization orientation of the analyzer, thereby obtaining the retardation value of the composite layer sample in the inclined state.

A retardation measuring apparatus according to the present invention comprises a light source part for applying a measuring beam to a measuring optical path, a sample holder holding a composite layer sample which is obtained by stacking a polarizing filter layer with a birefringent layer in the measuring optical path, an analyzer which is arranged and rotatably supported on a measuring beam outgoing side of the composite layer sample held on the sample holder, a compensation polarizing plate which is provided on a measuring beam incidence side of the composite layer sample held on the sample holder and rotatably supported independently of the analyzer for compensating polarization characteristics of the polarizing filter layer of the composite layer sample, a light receiving part for detecting intensity of light which is transmitted through the compensation polarizing plate, the composite layer sample and the analyzer, and an arithmetic and control unit for calculating retardation and an optical principal axis direction of the composite layer sample from the angle of rotation of the analyzer and the intensity of the transmitted light detected by the light receiving part.

A polarizer may be further arranged on the measuring beam incidence side of the compensation polarizing plate. In this case, the polarizer and the analyzer are rotatably supported, and they are kept in a prescribed polarization orientation relation such as a parallel Nicol state, for example, during rotation.

The compensation polarizing plate and the analyzer may be detachably arranged with respect to the measuring optical path. When the polarizer is provided, this polarizer may also be detachably arranged with respect to the measuring optical path.

In order to make it possible to evaluate visibility in the retardation measuring apparatus of the present invention, we use the sample holder comprising a mechanism for rotating the held composite layer sample in its plane, and an inclination mechanism for inclining the composite layer sample about a straight line along a surface of the composite layer sample.

According to the present invention, the term "composite layer" indicates a layer obtained by superposing films, sheets, plates or the like having or not having independence in direct contact with each other or indirectly (i.e., being interposing substances or spaces therebetween), and includes superposition of films, sheets, plates, or such different substances. Further, it is assumed that the term "stacking" includes not only a technique of fixedly or semi-fixedly pasting or bonding substances with each other with using an adhesive, a sticker or a sizing material or by fusion, but a technique of fixedly or temporarily superposing substances with each other in a prescribed positional relation with using a member such as Velcro tapes or with using electric/magnetic force, mechanical force or still another force.

Light applied from a light source for being used as a measuring beam is a white and unpolarized light which has no polarization characteristics.

When light is applied to a composite layer sample obtained by stacking a polarizing filter layer with a birefringent layer, such as a composite sheet prepared by pasting a polarizing film and a phase difference film to each other, for example, from the polarizing film side, linear polarized light of a constant direction is incident upon the phase difference film, so that light transmitted through the composite sheet is elliptically polarized.

When the degree of polarization of the polarizing film is insufficient, the polarizing film will not act as an ideal polarizing filter. In this case, when a compensation polarizing plate having a sufficiently high degree of polarization is arranged on a light incidence side of the polarizing film and polarized light transmission axes of the polarizing film and the compensation polarizing plate are kept in parallel with each other, the compensation polarizing plate compensates the characteristics of the polarizing film having a low degree of polarization. Therefore, it is possible to obtain the correct optical principal axis direction and/or the correct retardation value of the composite layer sample by measuring the relation between the polarization orientation of the analyzer and the intensity of the transmitted light, wherein the light transmitted through the compensating polarizing film and the composite layer sample passes through the analyzer and the analyzer rotates relatively with respect to the composite layer sample.

The optical principal axis direction and ellipticity of elliptic polarization of the light transmitted through the composite layer sample can be measured by relatively rotating the analyzer with respect to the composite layer sample, whereby the polarization transmission axis (and a polarization absorption axis perpendicular thereto) of the polarizing film and the retardation value and the optical principal axis direction of the phase difference film can be calculated from the results of the measurement. When a polarizer is arranged on the light incidence side of the compensation polarizing plate, the polarizer and the analyzer are synchronously rotated, and they are kept in a prescribed polarization orientation relation to each other, and these values can be calculated also. These calculations are described in detail with reference to embodiments.

According to the present invention, the compensation polarizing plate is arranged on the polarizing filter layer side of the composite layer sample which is obtained by stacking the polarizing filter layer with the birefringent layer and the polarization transmission axes of the polarizing filter layer and the compensation polarizing plate are kept in parallel with each other to compensate the polarization characteristics of the polarizing filter layer, whereby it is possible to measure the retardation value and the optical principal axis direction of the birefringent layer over a relatively wide wavelength range in sufficient accuracy even in case the polarizing filter layer is prepared from a material whose degree of polarization is not high. Thus, the present invention contributes to enlargement of the range of application of a birefringence measuring apparatus and reduction of the cost for manufacturing a liquid crystal display panel.

The higher the degree of polarization of the compensation polarizing plate, the better. However, the degree of polarization of the compensation polarizing plate not less than 99% is enough for measurement from considering accuracy levels of other parts of the retardation measuring apparatus. In measurement using such a compensation polarizing plate, the retardation value having a measurement error less than some nm and the optical principal axis direction having a measurement error less than 1° can be obtained.

It is possible to measure the retardation value and the optical principal axis direction of the birefringent layer by using an apparatus having a simple structure wherein the compensation polarizing plate is used and the intensity of the transmitted light can be measuered by simple rotation of the analyzer or by simple rotation of the polarizer and the analyzer. Therefore, the present invention is useful for both of step management of a production site bit on-line measurement and quality control of completed products.

It is possible to select retardation measurement of a conventional birefringent sample or a composite layer sample by altering the apparatus or recombining the elements of apparatus.

Even if the composite layer sample has a polarizing filter layer which is prepared from a material whose degree of polarization is not high, the angle of visibility can be evaluated as the retardation value, thereby it becomes easy to control the quality of a pasted product.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
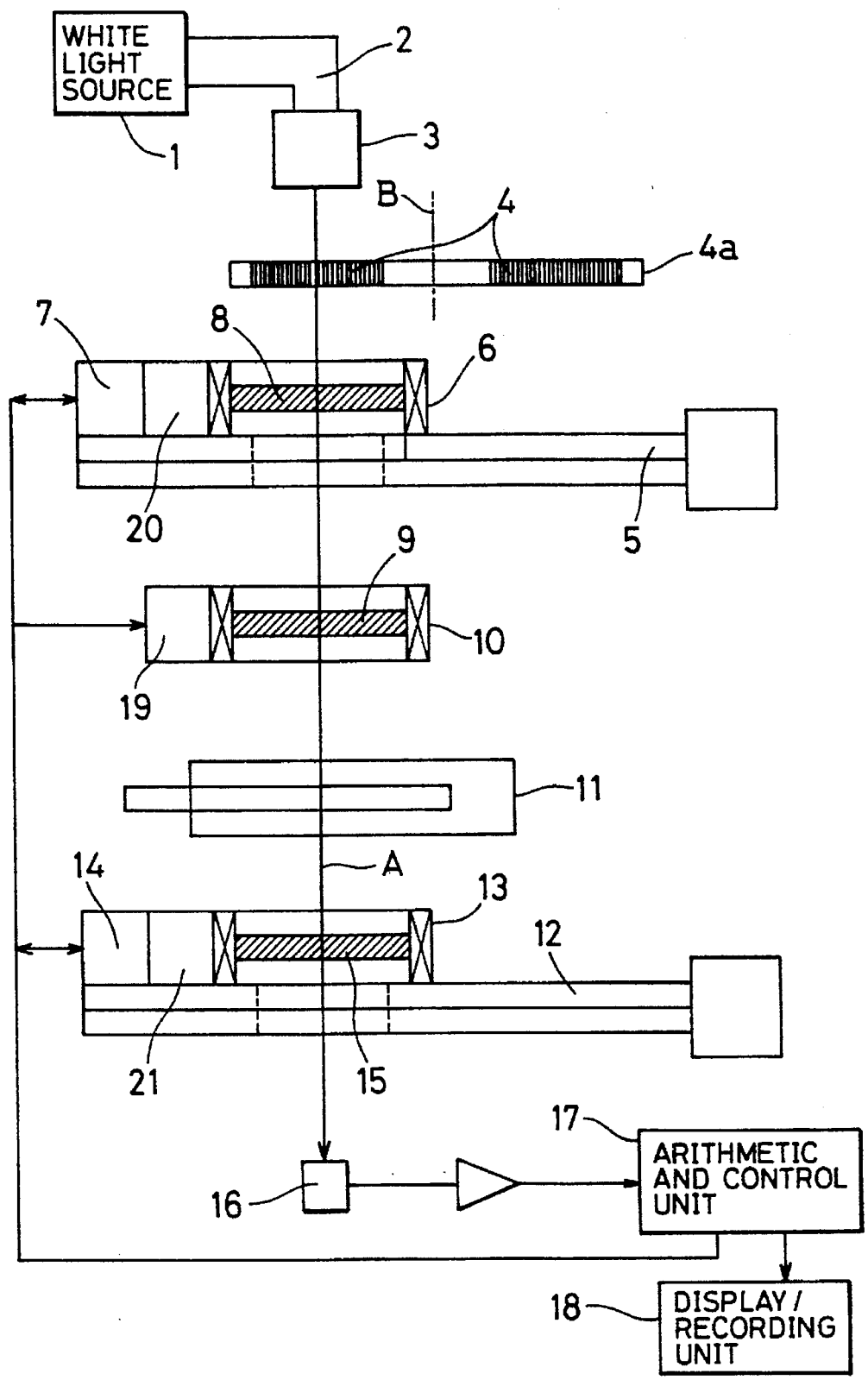
FIG. 1 is a schematic block diagram showing an apparatus according to an embodiment of the present invention.

FIG. 1 schematically shows the structure of an apparatus for measuring retardation of a composite layer sample according to an embodiment of the present invention.

Referring to FIG. 1, numeral 1 denotes a white light source, and numeral 2 denotes a light transmission path, which is prepared from an optical fiber bundle, for example. Numeral 3 denotes an optical system such as a condenser lens for obtaining a parallel beam from an output of the light transmission path 2. Numeral 4 denotes a filter part for transmitting light of a specific wavelength therethrough. A plurality of narrow-band interference filters having different transmission wavelengths are mounted on a disc 4a which is rotatable about an axis B, so that an arbitrary filter is selected and arranged on an optical path by rotation of the disc 4a. Light of a specific wavelength is selected from outgoing beams of the white light source 1 by switching of the filter, to be guided onto the optical path about an optical axis A.

A polarizer X stage 5 for advancing and retracting a polarizer 8 with respect to the optical axis A in a horizontal plane is provided on the optical axis A under the filter part 4. A polarizer θ stage 6 for rotating the polarizer 8, a motor 20 for driving rotation of the stage 6, and a rotation angle positioning encoder 7 for the polarizer 8 are mounted on the polarizer X stage 5, and the polarizer 8 is mounted on the polarizer θ stage 6.

Further, a compensation polarizing plate θ stage 10 for mounting and rotating a compensation polarizing plate 9, a sample holder 11, and an analyzer X stage 12 for advancing and retracting an analyzer 15 with respect to the optical axis A in a horizontal plane are successively provided on the optical axis A under the polarizer X stage 5. The compensation polarizing plate θ stage 10 is provided with a motor 19 for driving rotation of this stage 10, while an encoder for detecting the angle of rotation of the compensation polarizing plate 9 may be further provided. An analyzer θ stage 13 for rotating the analyzer 15 about the optical axis A, a motor 21 for driving rotation of the stage 13, and an encoder 14 for positioning the rotational angle of the analyzer 15 are provided on the analyzer X stage 12, and the analyzer 15 is mounted on the analyzer θ stage 13.

On the optical axis A, a photodetector 16 is further arranged under the analyzer 15, i.e., an outgoing side. The polarizer θ stage 6 and the analyzer θ stage 13 are controlled to be kept in a parallel Nicol state and to be synchronously rotated while angular position correction is carried out by an arithmetic and control unit 17 receiving angular position signals of the respective encoders 7 and 14. The motors 20 and 21 for rotating the polarizer 8 and the analyzer 15 are preferably stepping motors. In this case, the rotation may be temporarily stopped every time the motors 20 and 21 are rotated at a prescribed angle by control pulses from the arithmetic and control unit 17 to sample the output of the photodetector 16. Alternatively, it is also possible to sample the output of the photodetector 16 while the motors 20 and 21 are continuously rotating, since this sampling time is considerably short.

The inventive apparatus is also applicable to retardation measurement of a conventional sample which is not a composite layer sample. In retardation measurement of the ordinary sample, the compensation polarizing plate 9 is separated from the optical path and the X stages 5 and 12 are leftwardly advanced as shown in FIG. 1 to position the polarizer 8 and the analyzer 15 which are mounted on the stages on the optical path, so that the polarizer 8 and the analyzer 15 are rotated about the optical axis A while they are kept in a parallel Nicol relation to each other. In order to separate the compensation polarizing plate 9 from the optical path, the θ stage 10 may also be provided with an X stage for advancement and retraction which is similar to the X stage 5 or 12, or the θ stage 10 may be so formed that the compensation polarizing plate 9 can be attached to and detached from the θ stage 10.

In any case, the present invention is applicable to retardation measurement of a conventional sample and that of a composite layer sample prepared by stacking a polarizing film and a phase difference film by altering the apparatus or recombining the elements of apparatus.

The retardation of the composite layer sample can be measured whether the polarizer 8 is provided or not. In such measurement of the composite layer sample, a sample S is set on the sample holder 11 wherein a polarizing film side of the sample is directed toward the light source 1 (upper side in FIG. 1). In case the polarizer 8 is not mounted on the optical path, only the analyzer θ stage 13 is rotated during measurement of changing intensity of transmitted light. In case the polarizer 8 is mounted on the optical path, the polarizer θ stage 6 and the analyzer θ stage 13 are synchronously rotated during measurement of changing intensity of transmitted light.

These operations are elucidated more in detail hereafter. The arithmetic and control unit 17 for controlling the overall apparatus and processing measurement data carries out rotation control of the motor 19 for rotating the compensation polarizing plate 9. In case the polarizer 8 is not mounted on the optical path, the arithmetic and control unit 17 carries out feedback control to rotate the analyzer 15 by a signal from the encoder 14. In case the polarizer 8 is mounted on the optical path, the arithmetic and control unit 17 carries out feedback control by signals from the encoders 7 and 14 for synchronously rotating the polarizer rotating motor 20 and the analyzer rotating motor 21 to rotate the polarizer 8 and the analyzer 15. The arithmetic and control unit 17 incorporates the output of the photodetector 16 at constant angle spaces of the rotation of the analyzer 15, such as spaces of 1°, for example, to carry out data processing, calculates the retardation value of the sample etc., outputs the result to a display/recording unit 18 and makes display and/or print out the result.

If the degree of polarization of the polarizing film which is employed for a composite sheet of the composite layer sample less than 99%, it is important to use the compensation polarizing plate 9 to obtain accurate measurement for the retardation value and the optical principal axis of the phase difference film. In this case, the X stages 5 and 12 are first retracted to displace the polarizer 8 and the analyzer 15 from the optical path. The sample S is set on the sample holder 11 in a manner that the polarization film face thereof is directed upwardly, and the compensation polarizing plate 9 (degree of polarization: at least 99%) is rotated once to measure intensity of transmitted light, thereby obtaining either orthogonal positions or parallel positions of polarization transmission axes of the polarizing film of the composite sheet and the compensation polarizing plate. The orthogonal positions of the polarization transmission axes are positions where the amount of the transmission light is minimized while the parallel positions are those where the amount of transmitted light is maximized, and the orthogonal positions can be more correctly obtained. When the orthogonal positions of the polarization transmission axes are obtained, the compensation polarizing plate is rotated by 90°. In any case, the polarization transmission axes of the polarizing film and the compensation polarizing plate are superposed with each other in the same direction, to be in a parallel state.

Then, the X stage 12 is advanced to arrange the analyzer 15 on the optical path, and thereafter the analyzer 15 is rotated to measure change in intensity of the transmitted light by the photodetector 16, thereby calculating the direction of the transmission axis of the polarizing film which is a part of the composite sheet and the retardation value and the optical principal axis direction of the phase difference film.

Retardation calculation of the composite sheet is carried out as follows: First, description is made on the case of not employing polarizer 8.

Figure 2:
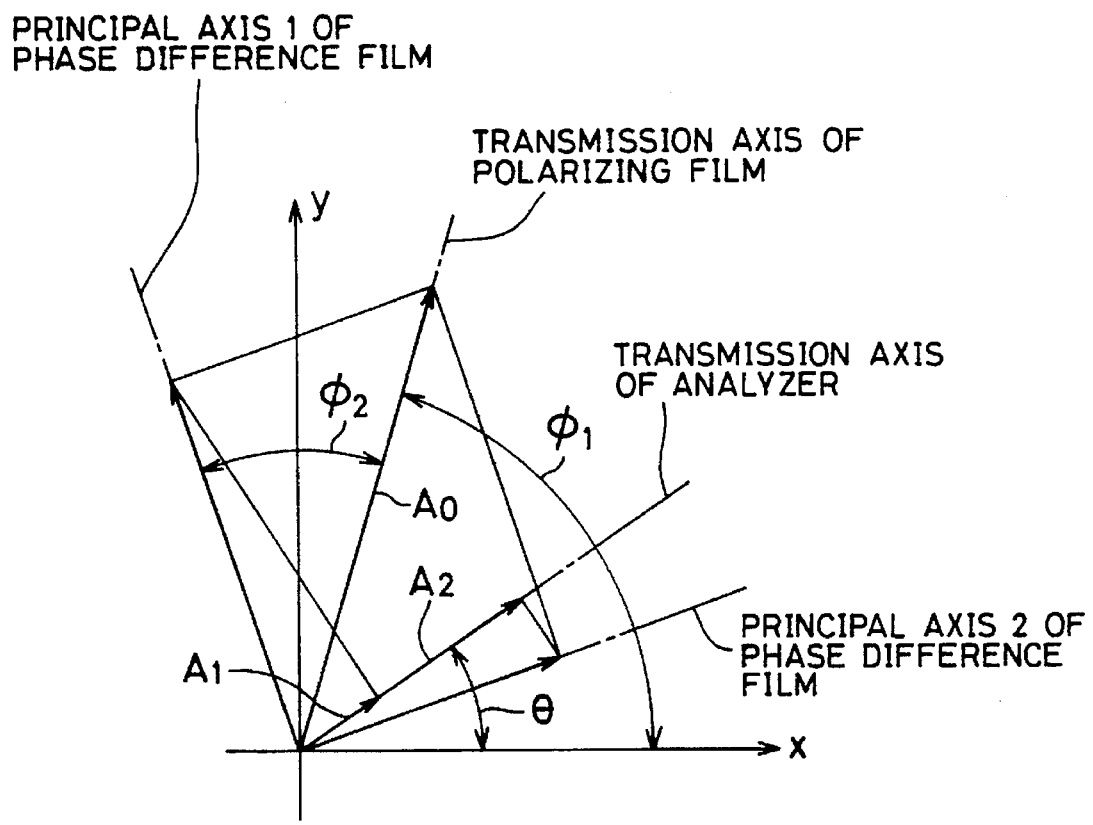
FIG. 2 illustrates the principle of the present invention.

It is assumed that $\lambda$ represents a wavelength for obtaining the retardation value of the sample, R represents the retardation value, $\phi_2$ represents an angle formed by the polarization transmission axis of the polarizing film forming the sample and an optical principal axis 1 (either one of two optical principal axes 1 and 2 which are perpendicular to each other) of the phase difference film, and $\phi_1$, represents an angle formed by the polarization transmission axis of the polarizing film and the coordinate axis (one direction in a plane perpendicular to the optical axis A: direction x in FIG. 2) of the apparatus. $\phi_1$ is measurable before this calculation and it is also possible to set the sample on the sample holder 11 in such a manner that $\phi_1$ is 0. However, in the following elucidation, it is assumed that $\phi_1$ is unknown in order to generally handle the operation of measurement.

It is assumed that $I(\theta)$ represents intensity of light transmitted through the composite sheet sample and the analyzer. $\theta$ represents the angle of rotation of the analyzer from a reference direction. Description is made with reference to FIG. 2. Since linearly polarized light transmitted through the polarizing film is incident upon the phase difference film of the sample, it is assumed that Io and Ao represent the intensity and amplitude of the linearly polarized light respectively. $A_0 \cdot \cos \phi_2$ represents the amplitude of a polarized component of the light, which is incident upon the phase difference film, along the optical principal axis 1, and $A_0 \cdot \sin \phi_2$ represents the amplitude of a polarized component along another optical principal axis 2. The components $A_1$ and $A_2$ which are components of the above mentioned components, respectively along the analyzer direction are as follows:

$$A_1 = A_0 \cos \phi_2 \cdot \cos (\phi_1 + \phi_2 - \theta)$$

$$A_2 = A_0 \sin \phi_2 \cdot \sin (\phi_1 + \phi_2 - \theta)$$

The light transmitted through the analyzer is a superposed beams of the aforementioned two components with phase difference $\delta$. The phase difference angle $\delta$ and the retardation R of the phase difference film are in the following relation:

$$2\pi R/\lambda = \delta$$

Assuming that A represents the amplitude of the light transmitted through the sample and the analyzer, A is expressed as follows by the cosine theorem:

$$\begin{aligned} A^2 &= I(\theta) \quad (1) \\ &= A_1^2 + A_2^2 - 2A_1 A_2 \cos \delta \\ &= A_0^2 \{\cos^2 \phi_2 \cdot \cos^2(\phi_1 + \phi_2 - \theta) + \sin^2 \phi_2 \cdot \sin^2(\phi_1 + \phi_2 - \theta) - \\ & \quad 2\cos\phi_2 \cdot \sin\phi_2 \cdot \cos(\phi_1 + \phi_2 - \theta)\sin(\phi_1 + \phi_2 - \theta)\cos\delta\} \end{aligned}$$

$A^2$ in the above equation is the output of the photodetector 16. $\cos \delta$ is to be obtained here, $I(\theta)$ and $\theta$ are directly obtained and $\phi_1$ and $\phi_2$ are unknown but constants, and the above equation is rewritten as follows, assuming that $\cos \phi_2 = K$, $\sin \phi_2 = L$ and $\phi_1 + \phi_2 - \theta = \Psi$:

$$I(\theta) = (K^2 \cos^2 \Psi + L^2 \sin^2 \Psi - 2KL \cos \Psi \sin \Psi \cos \delta) A_0^2$$

This is further rewritten as follows:

$$L^2 = 1 - K^2 \quad K^2 = 1 - L^2 \quad K^2 + L^2 = 1$$

Hence, the above equation becomes:

$$I(\theta) = (K^2 \cos^2 \Psi + (1-K^2) \sin^2 \Psi - KL \sin 2\Psi \cos \delta) A_0^2$$

and $$I(\theta) = \{(1-L^2) \cos^2 \Psi + L^2 \sin^2 \Psi - KL \sin 2\Psi \cos \delta\} A_0^2$$

These two equations are added up with each other and divided by 2, to obtain:

$$\begin{aligned} I(\theta) &= \{K^2 \cos^2\psi - \sin^2\psi) + \sin^2\psi - L^2(\cos^2\psi - \\ & \quad \sin^2\psi) + \cos^2\psi - 2KL\sin2\psi\cos\delta\}A_0^2/2 \\ &= \{(K^2 - L^2)\cos2\Psi - 2KL\sin2\Psi\cos\delta + 1\}A_0^2/2 \end{aligned}$$

From this equation, $I(\theta)$ performs one-cycle change during ½-rotation of the analyzer. In this equation, when $\sin 2\Psi = 0$, the maximum intensity of the transmitted light is obtainable. Similarly, where $\cos 2\Psi = 0$, the minimum one is obtainable, and hence:

$$I\ max = A_0^2 \cdot K^2$$

$$I\ min = A_0^2 (K^2 - 2KL \cos \delta)/2$$

Further, $K = \cos \phi_2$, $L = \sin \phi_2$, and hence L is eliminated from the above, to obtain:

$$I\ min = A_0^2\{1 - 2K(1-K^2)^{1/2} - \cos\delta\}/2$$

When $I max^{1/2}/Ao$ is substituted in K of Imin, $$\cos\delta = \{(A_0^2 - 2I\ min) - 2\ I\ max^{1/2}\ (A_0^2 - I\ max)^{1/2}\}/A_0^2$$

Thus, $\cos\delta$ can be obtained and hence the retardation R can be decided from $\cos\delta$.

In the above equations, $Ao^2$ represents the intensity of the light transmitted through the polarizing film of the sample. This value can be previously obtained as the maximum value of the output from the photodetector by setting the sample in the apparatus shown in FIG. 1 in a manner that the polarization film face thereof is directed upwardly during rotation of the analyzer. Since $K^2$ is obtainable from the afore-mentioned equation; $Imax = Ao^2 \cdot K^2$, the angle $\phi_2$ formed by the polarization transmission axis of the polarizing film of the sample and the optical principal axis 1 of the phase difference film can be obtained from the following definition of K; $K = \cos\phi_2$.

The above mentioned proceeding is an exemplary data processing method for obtaining the retardation according to the present invention, and the method of obtaining the retardation in practice is not restricted to the above one. For example, retardation and $\phi_2$ may be previously calculated by the above equation (1) with respect to various combinations of $Imin/Ao^2$ and $Imax/Ao^2$ to form a table, so that the retardation and $\phi_2$ of the sample are obtained from actually measured Imin and Imax by interpolation operations.

The operation in the aforementioned embodiment is carried out by rightwardly retracting the polarizer θ stage 6 which is mounted on the polarizer X stage 5 in the apparatus shown in FIG. 1 and separating the polarizer 8 from the optical path, and expression handling is simple. However, it is also possible to measure the retardation of the aforementioned composite sheet in a situation where the polarizer 8 is placed on the optical path. However, in this case expression handling is slightly complexed. Such an embodiment is now described. In this case, the X stages 5 and 12 are advanced to arrange the polarizer 8 and the analyzer 15 on the optical path, and thereafter the polarizer 8 and the analyzer 15 are synchronously rotated to measure change in intensity of the transmitted light by the photodetector 16, thereby calculating the direction of the transmission axis of the polarizing film of the composite sheet and the retardation value and the optical principal axis direction of the phase difference film.

The polarizer 8 and the analyzer 15 are brought into a parallel Nicol state. Employing the same symbols as the above, intensity I(θ) of light which is incident upon the photodetector 16 can be expressed as follows:

$$I(\theta) = A_0^2\{\cos^2\phi_2 \cdot \cos^2(\phi_1 + \phi_2 - \theta) + \qquad (2)$$
$$\sin^2\phi_2 \cdot \sin^2(\phi_1 + \phi_2 - \theta) -$$
$$2\cos\phi_2 \cdot \sin\phi_2 \cdot \cos(\phi_1 +$$
$$\phi_2 - \theta)\sin(\phi_1 + \phi_2 - \theta)\cos\delta\} \cdot \cos^2(\phi_1 - \theta)$$

In this equation, the term of $\cos^2(\phi_1 - \theta)$ is excessively applied to the equation (1).

Figure 3:
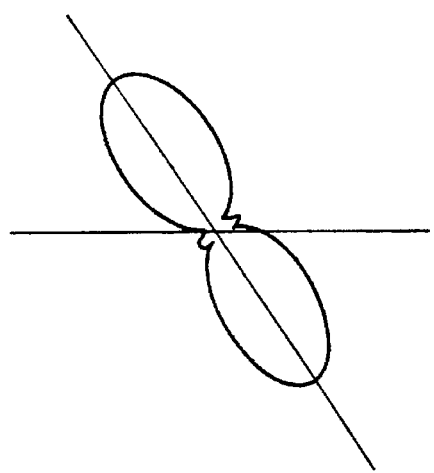
FIG. 3 is an explanatory graph showing transmitted light intensity in the present invention by polar coordinate indication.

Therefore, a polar coordinate graph may become not only a simple cocoon, elliptic or S shape but a four-leaved shape as shown in FIG. 3. Therefore, $\cos\delta$ cannot be simply obtained from the maximum and minimum values of I(θ) in general. It is a conventional method to actually measure I(θ) with respect to some θ values, substitute the results in the above equation and solve the obtained equation as simultaneous equations as to $\cos\delta$ and $\cos\phi_2$. In this case, the direction of the polarization transmission axis of the polarizing film part of the sample is measured and the sample should be set in a manner that the measured direction is as same as the reference direction x of the apparatus. Namely, handling of the equation is somewhat simplified when $\phi_1 = 0$.

In order to detect the direction of the polarization transmission axis of the polarizing film part, the polarizer 8 is displaced from the measuring optical path, so that the sample is set in a manner that the polarizing film side thereof is directed toward the analyzer, and when the intensity of the transmitted light is maximized, the direction of the rotated analyzer is obtained. The same direction can be obtained by adding 90° to a direction minimizing the intensity of the transmitted light. In place of carrying out the operation of solving the simultaneous equations, a polar coordinate graph of I(θ) may be calculated and formed by the above equation (2) as to various combinations of retardation values and $\phi_2$ values to schematically estimate the retardation and $\phi_2$ from the graph of actually measured I(θ), assume a polar coordinate graph by assuming the retardation and $\phi_2$, and repeat calculations to form an actually measured shape. This method is also applicable to the aforementioned embodiment. In any case, a concrete method of data processing implementing the principle of the inventive method is arbitrary.

In the aforementioned embodiments, the transmittance values of two axis directions of the part of the phase difference film of the sample are assumed to be equal to each other. However, in some case, the two transmittance values may be different from each other and in such a case the equations (1) and (2) can be calculated. Assuming that α (α<1 or α>1 depending on which one of two axis directions is assumed to be a denominator, it is assumed that α<1 now) presents the ratio of the transmittance values, the above equations (1) and (2) become the following equations (1') and (2') respectively:

$$I(\theta) = A_0^2\{\alpha^2\cos^2\phi_2 \cdot \cos^2(\phi_1 + \phi_2 - \theta) + \qquad (1')$$
$$\sin^2\phi_2 \cdot \sin^2(\phi_1 + \phi_2 - \theta) -$$
$$2\alpha\cos\phi_2 \cdot \sin\phi_2 \cdot \cos(\phi_1 + \phi_2 -$$
$$\theta)\sin(\phi_1 + \phi_2 - \theta)\cos\delta\}$$

$$I(\theta) = A_0^2\{\alpha^2\cos^2\phi_2 \cdot \cos^2(\phi_1 + \phi_2 - \theta) + \qquad (2')$$
$$\sin^2\phi_2 \cdot \sin^2(\phi_1 + \phi_2 - \theta) -$$
$$2\alpha\cos\phi_2 \cdot \sin\phi_2 \cdot \cos(\phi_1 + \phi_2 -$$
$$\theta)\sin(\phi_1 + \phi_2 - \theta)\cos\delta\} \cdot \cos^2(\phi_1 - \theta)$$

In the above equation, measuring accuracy is further improved when $\phi_1$ is stepwisely changed in several stages within the range from a little smaller value than an initially obtained value to a little bigger value than one, $\phi_2$ and R are operated every $\phi_1$ value and values of $\phi_1$, $\phi_2$ and R are decided finally so that convergence values of remainders are minimized in determination of the retardation R of the composite layer sample in relation to the polarization transmission axis direction $\phi_1$ of the polarizing film of the composite sheet and the angle $\phi_2$ formed by the polarization transmission axis direction and the optical principal axis 1 direction of the phase difference film.

Figure 4:
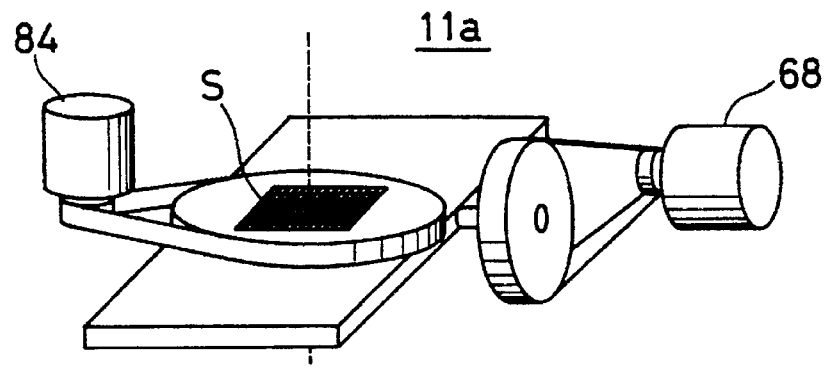
FIG. 4 is a schematic perspective view showing a sample holder according to another embodiment of the present invention.
Figure 5:
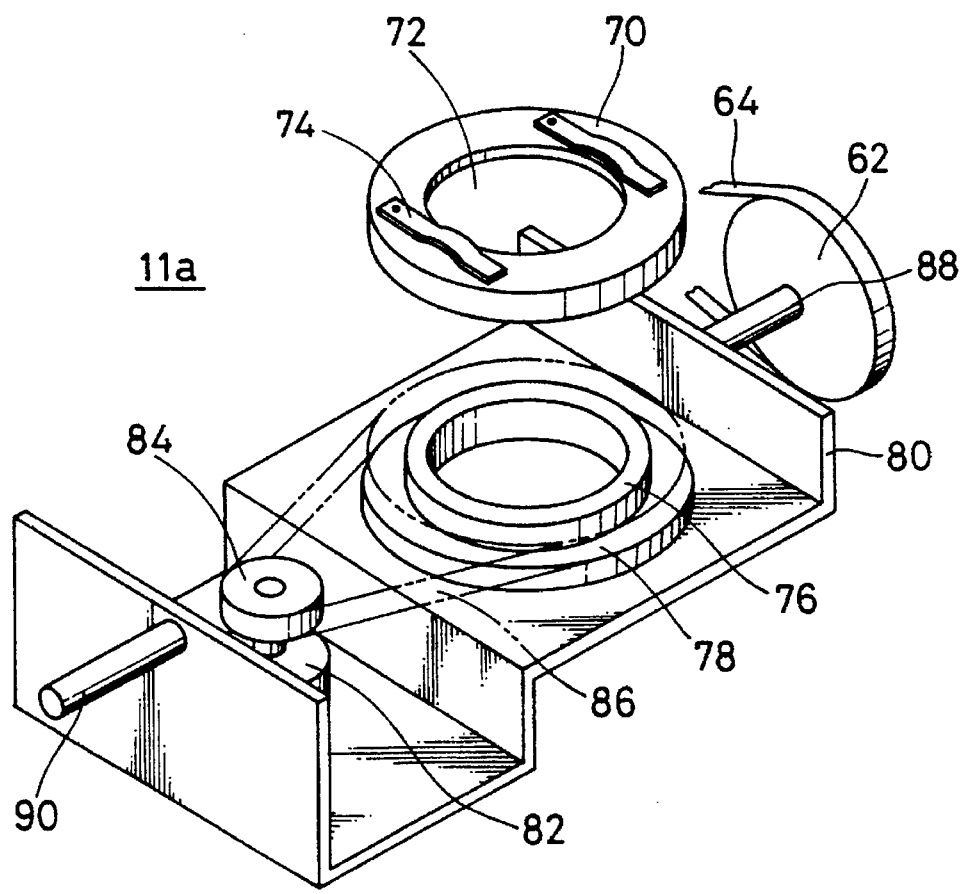
FIG. 5 is an exploded perspective view showing the sample holder in detail.

The above-mentioned embodiments are described on the assumption that the sample holder 11 holds the composite layer sample S in a manner that its surface is perpendicular to the optical axis A. In order to evaluate the angle of visibility of the composite layer sample S, the sample holder 11 must be capable of rotating the composite layer sample S in its plane and inclining the sample about a straight line along the surface of the composite layer sample S. FIG. 4 shows an example of such a sample holder 11a, and FIG. 5 shows the sample holder 11a in detail. A sample holding part 70 is provided with a hole 72 in its center, and its rear surface is hollowed out in the form of a ring to define a concave part, presser plates 74 for pressing and holding a sample are provided in two portions on the upper surface of the sample holding part 70. A rotary table 78 having a ring-shaped convex portion 76 which engages with the concave portion on the rear surface of the sample holding part 70 is mounted on a substrate 80, to rotatably hold the sample holding part 70 about an axis which is perpendicular to a sample surface. A belt 86 is mounted between a side surface of the sample holding part 70 which is fitted in the rotary table 78 and a pulley 84 which is mounted on a rotary shaft of a stepping motor 82, so that the sample holding part 70 is rotated by the motor 82. The motor 82 is also mounted on the substrate 80, and mounting surfaces of the motor 82 and the rotary table 78 are so formed that the pulley 84 and the sample holding part 70 are arranged in the same plane. Shafts 88 and 90 are mounted on a pair of side surfaces of the substrate 80, so that central axes of the shafts 88 and 90 are on the surface of the sample holding part 70. These shafts 88 and 90 are supported by a measuring apparatus body. A pulley 62 is mounted on the shaft 88, and a belt 64 is extended across a pulley 66 of a stepping motor 68 which is provided on the measuring apparatus body side and this pulley 62, so that the substrate 80 is inclined by the motor 68.

An arithmetic and control unit 17 also controls the motors 68 and 82.

The sample holder 11a shown in FIGS. 4 and 5 is employed for measuring the angle of visibility of a composite layer sample, in the following manner: First, a composite layer sample S is mounted on the sample holding part 70 so that its surface is perpendicular to an optical axis A, and an analyzer 15 is rotated once to calculate retardation R and an optical principal axis direction of the composite layer sample S.

Then, the motor 82 is driven to rotate the composite layer sample S in its plane so that either one of two optical principal axis directions is along the direction of the central axis (inclination axis) of the shafts 88 and 90. Then, the motor 68 is driven to incline the sample holding part 70 about its inclination axis by a constant angle of about 10 degrees, for example, and the analyzer 15 is again rotated once to calculate the retardation R of the composite layer sample S. Thus, the retardation is obtained while changing the inclination of the composite layer sample S.

The arithmetic and control unit 17 reads the angle of inclination of the sample holding part 70 by a driving pulse of the motor 68.

EXPERIMENTAL EXAMPLE 1 a) In the apparatus having the structure shown in FIG. 1, a polarizing plate (referred to as a polarizing plate B) having a degree of polarization of 95.0% was fixed to the sample holder 11 so that an angle formed by its polarization transmission axis and the coordinate axis x of the apparatus was 90 degrees, and a phase difference film was stacked on this polarizing plate so that its optical principal axis was at 30 degrees ($\phi_2$) with respect to the polarization transmission axis of the polarizing plate, to form a composite sheet material. The polarizer 8 and the analyzer 15 were placed on the optical path, kept in a parallel Nicol relation to each other and synchronously rotated, to measure intensity of transmitted light every rotation of 10 degrees. An angle $\phi_1$ formed by the polarization transmission axis of the polarizing plate of the composite sheet and the coordinate axis x of the apparatus, an angle $\phi_2$ (deg.) formed by the polarization transmission axis of the polarizing plate and the optical principal axis of the phase difference film, and the retardation value R of the phase difference film were calculated from the results of the measurement.

The same measurement was made on nine types of phase difference films by exchanging only the phase difference film every measurement of a single sample and employing the same polarizing plate in common. Table 1 shows the results. Ro represents the retardation values of the nine types of the phase difference films.

b) In the apparatus having the structure shown in FIG. 1, a compensation polarizing plate (degree of polarization: 99.9%) 9 (referred to as a polarizing plate A) was placed on the light incidence side of a sample with respect to the same composite sheet sample as the above a) as shown in the figure, and the compensation polarizing plate 9 was rotated on the optical path in a state separating the polarizer 8 and the analyzer 15 from the optical path to detect change in intensity of transmitted light, and the polarization transmission axis of the compensation polarizing plate 9 was set to be in parallel with that of a polarizing plate of the sample. An angle $\phi_1$ (deg.) formed by the orientation of the polarization transmission axis of the polarizing plate of the composite sheet and the coordinate axis x of the apparatus was obtained from the rotational angle position of the compensation polarizing plate 9.

The polarization transmission axes of the compensation polarizing plate 9 and the polarizing plate of the sample were kept in parallel with each other. The polarizer 8 and the analyzer 15 were returned onto the optical path, both were synchronously rotated while being kept in a parallel Nicol relation to each other, intensity of transmitted light was measured every rotation of 10 degrees, and an angle $\phi_2$ (deg.) formed by the optical principal axis of a phase difference film with respect to the polarization transmission axis of the polarizing plate of the composite sheet and the retardation value R of the phase difference film were calculated from the results of the measurement.

The same measurement was made on nine types of phase difference films by exchanging only the phase difference film on every measurement of a single sample and employing the same polarizing plate in common. Table 1 shows the results in correspondence to the above a).

TABLE 1

| Sample | $R_0$ | a) Without compensation polarizing plate | | | b) With compensation polarizing plate | | |
|---|---|---|---|---|---|---|---|
| | | R | $\phi_1(°)$ | $\phi_2(°)$ | R | $\phi_1(°)$ | $\phi_2(°)$ |
| 1 | 152.5 | 124.0 | 84 | −44 | 153.0 | 90 | −31 |
| 2 | 218.7 | 196.0 | 86 | −32 | 220.4 | 90 | −28 |
| 3 | 241.2 | 223.5 | 87 | −31 | 243.3 | 90 | −30 |
| 4 | 271.9 | 261.7 | 89 | −30 | 266.2 | 90 | −30 |
| 5 | 362.3 | 350.7 | −88 | −27 | 367.0 | 90 | −30 |
| 6 | 382.9 | 365.0 | −87 | −25 | 386.8 | 90 | −30 |
| 7 | 413.4 | 393.0 | −86 | −24 | 417.7 | 90 | −30 |
| 8 | 395.0 | 378.1 | −87 | −25 | 400.9 | 90 | −30 |
| 9 | 416.8 | 393.1 | −86 | −23 | 423.1 | 90 | −30 | c) Comparing the results of a) and b) with each other, there were remarkable errors of 5% on the average and about 20% at the maximum in the measuring retardation values R when the compensation polarizing plate was not employed, and there were also considerably large errors of about 5 degrees on the average and 14 degrees at the maximum in measuring the optical principal axis direction $\phi_2$.

When the compensation polarizing plates was employed, on the other hand, the retardation values R were with errors of not more than ±2% and 1.4% on the average, and errors were hardly caused in the optical principal axis direction $\phi_2$. Thus, it has been proved possible to ensure sufficient accuracy and reliability according to the present invention also in a composite sheet employing a polarizing film having an inferior degree of polarization.

Measurements using a polarizing plate having a degree of polarization of 99.9% in place of the polarizing plate B were also carried out in the same way as the above a) and b). The results showed that the retardation values R and the optical principal axis direction $\phi_2$ were obtained with high accuracy in the measurements of a) and b).

EXPERIMENTAL EXAMPLE 2

Measurements similar to that in a) of Experimental Example 1 were carried out on the same composite sheets as those in Experimental Example 1 in a state of separating the polarizer 8 and the compensation polarizing plate 9 from the optical path in the structure shown in FIG. 1, and measurements similar to those in b) were carried out in a state of placing the compensation polarizing plate 9 on the optical path. Table 2 shows the results.

TABLE 2

| | | a) Without compensation polarizing plate | | | b) With compensation polarizing plate | | |
|---|---|---|---|---|---|---|---|
| Sample | $R_0$ | R | $\phi_1(°)$ | $\phi_2(°)$ | R | $\phi_1(°)$ | $\phi_2(°)$ |
| 1 | 152.5 | 153.0 | 89 | 30 | 152.0 | 89 | −31 |
| 2 | 218.7 | 219.7 | 89 | 29 | 218.7 | 90 | 29 |
| 3 | 241.2 | 238.7 | 90 | 29 | 246.0 | 89 | 31 |
| 4 | 271.9 | 260.6 | 90 | 30 | 273.1 | 89 | 31 |
| 5 | 362.3 | 364.7 | 89 | 31 | 363.8 | 90 | 30 |
| 6 | 382.9 | 385.1 | 89 | 30 | 385.9 | 90 | 30 |
| 7 | 413.4 | 415.1 | 90 | 29 | 417.1 | 90 | 30 |
| 8 | 395.0 | 397.6 | 90 | 29 | 397.1 | 90 | 30 |
| 9 | 416.8 | 419.5 | 90 | 29 | 420.8 | 89 | 31 |

As shown in Table 2, there were considerable errors of up to about 4% in the retardation values when compensation polarizing plate was not employed and errors of about 1 degree on the average were caused in the optical principal axis direction, in contast the errors of the retardation values were within ±1% when the compensation polarizing plate was employed and errors were hardly caused as 0.3% on the average as to the optical principal axis direction. When the polarizer was not employed, difference depending on presence/absence of the compensation plate was not so remarkable as Experimental Example 1 employing the polarizers, but this difference remarkably appears at some range of the measuring wavelength.

Measurements using a polarizing plate having a degree of polarization of 99.9% in place of the polarizing plate B were also carried out in the same way as the above a) and b). The results showed that the retardation values R and the optical principal axis direction $\phi_2$ were obtained with high accuracy in the measurements of a) and b).

EXPERIMENTAL EXAMPLE 3

Figure 6A:
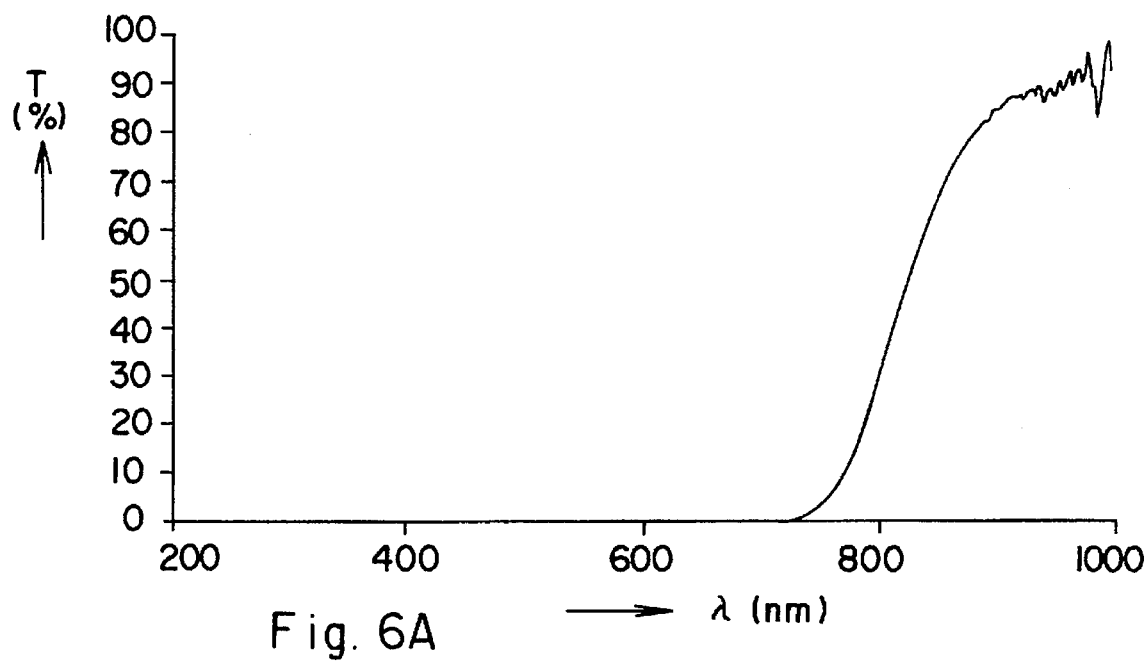
FIGS. 6A and 6B are spectral maps showing spectral transmission characteristics of polarizing filters having high and low degrees of polarization respectively.
Figure 6B:
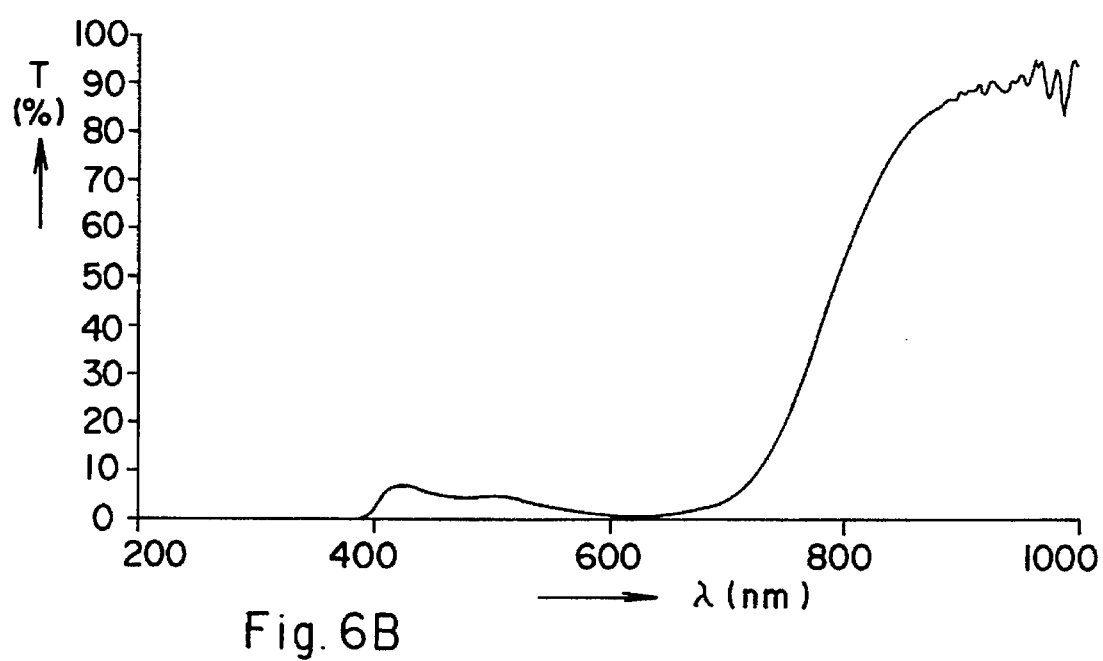

FIGS. 6A and 6B show spectral transmission characteristics of the compensation polarizing plate (degree of polarization: 99.9%) (polarizing plate A) and the polarizing plate (degree of polarization: 95.0%) (polarizing plate B) of the composite layers employed in Experimental Examples 1 and 2 in the case of arranging the polarizers in orthogonal Nicol states with respect to the polarizing plates A and B respectively.

Transmitted light is not detected in a wavelength region of not more than 700 nm in the polarizing plate A in contrast there exists transmitted light also below 700 nm in the polarizing plate B. The transmittance is at a small value of about 1% in the range of 570 to 640 nm, and transmittance of several percent is caused in the range of 400 to 550 nm. The degree of polarization of 95% indicates that average transmittance in orthogonal Nicol arrangement in the wavelength region of 400 to 800 nm is 5%, for example.

Since the measuring beam wavelength in Experimental Examples 1 and 2 was 590 nm, the transmittance in orthogonal Nicol arrangement is small and hence the difference between the case of employing the compensation polarizing plate and the case of not employing the same is relatively small, therefore it is presumed that the difference therebetween is considerably increased when a measuring beam of another wavelength such as 500 nm, for example, is employed.

Thus, it can be said that the present invention employing the compensation polarizing plate has an effect capable of making precise measurement over a wide wavelength range.

EXPERIMENTAL EXAMPLE 4

Example of measuring the angle of visibility of a composite layer sample is described.

The apparatus shown in FIG. 1 and the sample holder shown in FIGS. 4 and 5 were used, and the two types of phase difference films and two composite sheets using these films are measured as samples.

In two optical principal axes of two types of phase difference films A and B having retardation values of 393.8 nm and 584.1 nm respectively, the optical principal axis having a larger refractive index was inclined as the inclination axis to make angles of incidence of measuring beams differ from each other and retardation values were measured.

Polarizing films having transmittance values of about 44% were superposed on the two types of phase difference films to form respective composite sheets having angles of about 35° formed by the optical principal axes of the phase difference films and polarization absorption axes of polarizing films as the samples. As to the composite sheet samples, the compensation polarizing plate was employed, polarization transmission axis of the polarizing film and the compensation polarizing plate was kept in parallel with each other to compensate polarization characteristics of polarizing filter layers, and an optical principal axis having a larger refractive index of the phase difference film was inclined as the inclination axis similarly to the case of measuring the phase difference films, to measure retardation values at the various angles of incidence of measuring beams. Table 3 shows the results.

TABLE 3

| Angle of incidence | Phase difference film A | | Phase difference film B | |
| --- | --- | --- | --- | --- |
| | Single | Superposed | Single | Superposed |
| 0° | 393.8 nm | 394.1 nm | 584.1 nm | 587.9 nm |
| 10° | 399.2 | 399.2 | 587.7 | 591.2 |
| 20° | 413.1 | 414.1 | 599.1 | 603.5 |
| 30° | 435.1 | 438.0 | 612.2 | 617.5 |
| 40° | 464.4 | 467.6 | 639.8 | 618.3 |

It is understood from the results shown in Table 3 that the composite sheets also showed retardation values substantially coincident with those of the case of measuring the phase difference films singly, and the angle of visibility can be evaluated also as to a pasted product of an optical film. Consequently, the present invention can be applied to shipping tests in an optical film pasting/working maker and receiving tests in a panel maker, to contribute to stabilization in quality of pasted products.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of measuring retardation of a composite layer, comprising the steps of:

providing a composite layer sample, being obtained by stacking a polarizing filter layer with a birefringent layer, with a compensation polarizing plate on the side of said polarization filter layer and keeping polarization transmission axes of said polarizing filter layer and said compensation polarizing plate in parallel with each other thereby compensating polarization characteristics of said polarizing filter layer; and applying a measuring beam from the side of said compensation polarizing plate for passing light being transmitted through said compensation polarizing plate and said composite layer sample through an analyzer and relatively rotating the polarization transmission axis of said analyzer with respect to those of said compensation polarizing plate and said composite layer sample for detecting the relation between intensity of said light being transmitted through said analyzer and the polarization orientation of said analyzer thereby obtaining retardation and the optical principal axis direction of said composite layer sample.

2. The method of measuring retardation in accordance with claim 1, wherein said compensation polarizing plate has a degree of polarization not less than 99%.

3. The method of measuring retardation in accordance with claim 1, wherein said measuring beam is applied in unpolarized condition to said compensation polarizing plate.

4. The method of measuring retardation in accordance with claim 1, wherein a polarizer is arranged on a light incidence side of said compensation polarizing plate, said polarizer being maintained in a prescribed polarization orientation relation with said analyzer.

5. The method of measuring retardation in accordance with claim 1, wherein said intensity of said transmitted light is measured during one relative rotation of said compensation polarizing plate to said polarizing filter layer in a state arranging neither a polarizer nor said analyzer on an optical path, thereby bringing said polarization transmission axes of said polarizing filter layer and said compensation polarizing plate into parallel positions with each other from the result of the measurement.

6. The method of measuring retardation in accordance with claim 5, wherein said intensity of said transmitted light is measured during said one relative rotation of said compensation polarizing plate for obtaining orthogonal positions of said polarization transmission axes of said polarizing filter layer and said compensation polarizing plate, and thereafter said compensation polarizing plate is rotated relatively to said polarizing filter layer by 90° for bringing said polarization transmission axes of said polarizing filter layer and said compensation polarizing plate into parallel positions.

7. The method of measuring retardation in accordance with claim 1, further comprising steps of:

arranging a surface of said composite layer sample in a perpendicular state with respect to an optical path of said measuring beam for obtaining said retardation and said optical principal axis direction of said composite layer sample, and thereafter relatively rotating said polarization transmission axis of said analyzer with respect to that of said composite layer sample again in a state of inclining said surface of said composite layer sample along an inclination axis of either one of obtained said two optical principal axis directions for detecting the relation between said intensity of said light being transmitted through said analyzer and said polarization orientation of said analyzer thereby obtaining said retardation of said composite layer sample.

8. An apparatus for measuring retardation of a composite layer, comprising:

a light source part for applying a measuring beam to a measuring optical path;

a sample holder holding a composite layer sample being obtained by stacking a polarizing filter layer with a birefringent layer in said measuring optical path;

an analyzer being arranged and rotatably supported on a measuring beam outgoing side of said composite layer sample being held on said sample holder;

a compensation polarizing plate being provided on a measuring beam incidence side of said composite layer sample being held on said sample holder and rotatably supported independently of said analyzer for compensating polarization characteristics of said polarizing filter layer of said composite layer sample, a polarization axis of said compensating polarizing plate being arranged in parallel with a polarization axis of said polarizing filter layer of said composite layer sample in said sample holder;

a light receiving part for detecting intensity of light being transmitted through said analyzer through said compensation polarizing plate and said composite layer sample; and an arithmetic and control unit for calculating retardation and a optical principal axis direction of said composite layer sample from the angle of rotation of said analyzer and said intensity of said transmitted light being detected by said light receiving part.

9. The apparatus for measuring retardation in accordance with claim 8, wherein a polarizer is further arranged on said measuring beam incidence side of said compensation polarizing plate, said polarizer and said analyzer being rotatably supported while keeping a prescribed polarization orientation relation with each other.

10. The apparatus for measuring retardation in accordance with claim 9, wherein said compensation polarizing plate, said analyzer and said polarizer are structured to be detachable independently from said measuring optical path.

11. The apparatus for measuring retardation in accordance with claim 8, wherein said compensation polarizing plate and said analyzer are structured to be detachable independently from said measuring optical path.

12. The apparatus for measuring retardation in accordance with claim 8, where in said sample holder comprises a mechanism for rotating said composite layer sample held in its plane, and an inclination mechanism of inclining said composite layer about a straight line along a surface of said composite layer sample.

* * * * *